(12) United States Patent
Pacetti

(10) Patent No.: US 9,585,777 B2
(45) Date of Patent: Mar. 7, 2017

(54) IMPLANTABLE PROSTHESIS WITH RADIOPAQUE PARTICLES AND METHOD OF MAKING SAME

(71) Applicant: Abbott Cardiovascular Systems Inc., Santa Clara, CA (US)

(72) Inventor: Stephen Pacetti, San Jose, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

(21) Appl. No.: 14/858,355

(22) Filed: Sep. 18, 2015

(65) Prior Publication Data

US 2016/0030211 A1 Feb. 4, 2016

Related U.S. Application Data

(62) Division of application No. 13/533,728, filed on Jun. 26, 2012, now Pat. No. 9,155,645.

(51) Int. Cl.
| | |
|---|---|
| *A61F 2/82* | (2013.01) |
| *A61F 2/89* | (2013.01) |
| *A61F 2/91* | (2013.01) |
| *A61F 2/915* | (2013.01) |
| *A61L 31/02* | (2006.01) |
| *A61L 31/16* | (2006.01) |
| *A61L 31/18* | (2006.01) |
| *A61K 49/04* | (2006.01) |

(52) U.S. Cl.
CPC ............... *A61F 2/89* (2013.01); *A61F 2/915* (2013.01); *A61K 49/04* (2013.01); *A61L 31/022* (2013.01); *A61L 31/16* (2013.01); *A61L 31/18* (2013.01); *A61F 2002/91566* (2013.01); *A61F 2230/0069* (2013.01); *A61F 2240/001* (2013.01); *A61F 2250/0067* (2013.01); *A61F 2250/0068* (2013.01); *A61F 2250/0098* (2013.01)

(58) Field of Classification Search
CPC ................. A61F 2/82; A61F 2/91; A61F 2/89
See application file for complete search history.

(56) References Cited

U.S. PATENT DOCUMENTS

| | | | |
|---|---|---|---|
| 2010/0145437 A1 | 6/2010 | Girton et al. | |
| 2011/0245905 A1* | 10/2011 | Weber ................. | A61L 31/044 623/1.15 |
| 2012/0067008 A1* | 3/2012 | Bienvenu ............. | A61L 31/121 53/452 |

* cited by examiner

*Primary Examiner* — Jason-Dennis Stewart
(74) *Attorney, Agent, or Firm* — Squire Patton Boggs (US) LLP

(57) ABSTRACT

An implantable prosthesis can comprise a strut having a lumen, radiopaque particles within the lumen, and a polymer binder. The polymer binder retains the radiopaque particles within the lumen. The strut may have side holes through which a therapeutic agent may pass and through which the radiopaque particles are incapable of passing. The polymer binder may be absent or optional. The radiopaque particles can have sizes that prevent them from escaping out of the lumen through the side holes. The radiopaque particles placed within the lumen can improve visualization of the prosthesis during an implantation procedure.

9 Claims, 6 Drawing Sheets

IMPLANTABLE PROSTHESIS WITH RADIOPAQUE PARTICLES AND METHOD OF MAKING SAME

CROSS-REFERENCE TO RELATED APPLICATION

This application is a divisional application Ser. No. 13/533,728, filed Jun. 26, 2012, which application is hereby incorporated by reference.

FIELD OF THE INVENTION

This invention relates generally to implantable medical devices and, more particularly, an implantable prosthesis and a method of making an implantable prosthesis.

BACKGROUND OF THE INVENTION

Drug-filled stents have been presented as an alternative or complement to conventional drug-coated stents with a coating of drug-polymer or pure drug. With drug-filled stents, the stent struts have a drug-filled center. An example of a stent strut having a drug-filled center is described in US Publication No. 2011/0008405, entitled "Hollow Tubular Drug Eluting Medical Devices," which is incorporated herein by reference in its entirety for all purposes. After implantation, the drug is released out of holes formed in the stent struts. The drug contained within the stent struts is protected from potential damage when the stent is crimped onto a carrier device, such as a balloon catheter, and during the process of positioning the stent and catheter through a patient's vasculature to a target treatment site.

A visualization method that relies on the radiopacity of the stent is often used to determine whether the stent is properly located at the target treatment site. The struts of drug-filled stents may be less radiopaque as they are hollow compared to conventional drug-coated stents having only solid metal wire struts. The reduction in radiopacity can make it difficult to visualize the stent. Accordingly, there is a need to improve radiopacity of drug-filled stents.

SUMMARY OF THE INVENTION

Briefly and in general terms, the present invention is directed to an implantable prosthesis and method of making an implantable prosthesis.

In aspects of the present invention, an implantable prosthesis comprises a strut having a lumen, radiopaque particles within the lumen, and a polymer binder within the lumen, the polymer binder surrounding the radiopaque particles and retaining the radiopaque particles in the lumen.

In other aspects, the radiopaque particles are not bonded directly to each other and the polymer binder is located between and separates the radiopaque particles.

In other aspects, the polymer binder prevents the radiopaque particles from escaping through holes in the strut.

In other aspects, the implantable prosthesis further comprises a therapeutic agent within the lumen, wherein the polymer binder carries or is combined with the therapeutic agent.

In other aspects, the strut includes a metal layer surrounding the lumen, and the metal layer includes a plurality of side holes for releasing the therapeutic agent.

In other aspects, surface areas of the metal layer between the side holes are non-porous with respect to the therapeutic agent.

In other aspects, the polymer binder allows the therapeutic agent to diffuse or elute out of the polymer binder and escape out of the side holes of the metal layer while the polymer binder simultaneously prevents the radiopaque particles from escaping out of the side holes of the metal layer.

In other aspects, the polymer binder prevents the radiopaque particles from shifting in position within the lumen.

In other aspects, the radiopaque particles include a mixture of a radiopaque material and an internal binder.

In aspects of the present invention, a method comprises placing radiopaque particles within a lumen of a strut, and retaining the radiopaque particles in the lumen using a polymer binder in the lumen.

In other aspects, the radiopaque particles are not bonded directly to each other and the polymer binder is located between and separates the radiopaque particles.

In other aspects, after the placing of radiopaque particles within the lumen of the strut, the polymer binder prevents the radiopaque particles from escaping through side holes in the strut.

In other aspects, the placing of radiopaque particles within the lumen includes passing the radiopaque particles through an end hole of the strut, the end hole being in communication with the lumen.

In other aspects, the placing of radiopaque particles within the lumen includes passing the radiopaque particles through side holes of the strut.

In other aspects, the placing of radiopaque particles within the lumen includes placing a mixture of the radiopaque particles and the polymer binder into the lumen.

In other aspects, the method further comprises introducing a therapeutic agent into the lumen, wherein the therapeutic agent is disposed between the radiopaque particles.

In other aspects, the introducing of the therapeutic agent into the lumen is performed simultaneously with the placing of the radiopaque particles in the lumen.

In other aspects, the lumen is surrounded by a metal layer of the strut, and the method further comprises forming side holes at predetermined locations through the metal layer, and the side holes allow the therapeutic agent to be introduced into the lumen or released out from the lumen or both introduced into and released out from the lumen.

In other aspects, the introducing of the therapeutic agent into the lumen includes allowing the therapeutic agent to pass through side holes of the strut and infuse or be absorbed into the polymer binder in the lumen.

In other aspects, the introducing of the therapeutic agent into the lumen includes introducing a mixture of the therapeutic agent, the polymer binder, and the radiopaque particles into the lumen.

In other aspects, the introducing of the mixture includes introducing the mixture through an end hole of the strut, the end hole being in communication with the lumen.

In other aspects, the introducing of the mixture includes introducing the mixture through side holes of the strut.

In aspects of the present invention, an implantable prosthesis comprises a strut having a lumen and a plurality of side holes extending from the lumen to an exterior surface of the strut, and radiopaque particles within the lumen, the radiopaque particles having sizes that prevent the radiopaque particles from passing through the side holes.

In other aspects, the strut has an end hole for placing the radiopaque particles within the lumen.

In other aspects, the end hole is in communication with the lumen, and the lumen passes through all struts of the prosthesis.

In other aspects, the implantable prosthesis further comprises a therapeutic agent in the lumen. The therapeutic agent is capable of escaping from the lumen through the side holes.

In other aspects, the implantable prosthesis further comprises a carrier substance within the lumen, the carrier substance carrying the therapeutic agent, wherein the therapeutic agent is capable of diffusing or eluting out of the carrier substance.

In aspects of the present invention, a method comprises placing radiopaque particles within a lumen of a strut having a plurality of side holes extending from the lumen to an exterior surface of the strut. The radiopaque particles have sizes that prevent the radiopaque particles from passing through the side holes.

In other aspects, the placing of the radiopaque particles within the lumen includes introducing the radiopaque particles through an end hole of the strut.

In other aspects, the method further comprises crimping, sealing or plugging the end hole after the introducing of the radiopaque particles through the end hole.

In other aspects, the method further comprises forming the side holes through the strut before the introducing of the radiopaque particles through the end hole.

In other aspects, the method further comprises forming the side holes through the strut after the introducing of the radiopaque particles through the end hole.

The features and advantages of the invention will be more readily understood from the following detailed description which should be read in conjunction with the accompanying drawings.

DETAILED DESCRIPTION OF EXEMPLARY EMBODIMENTS

Figure 1:
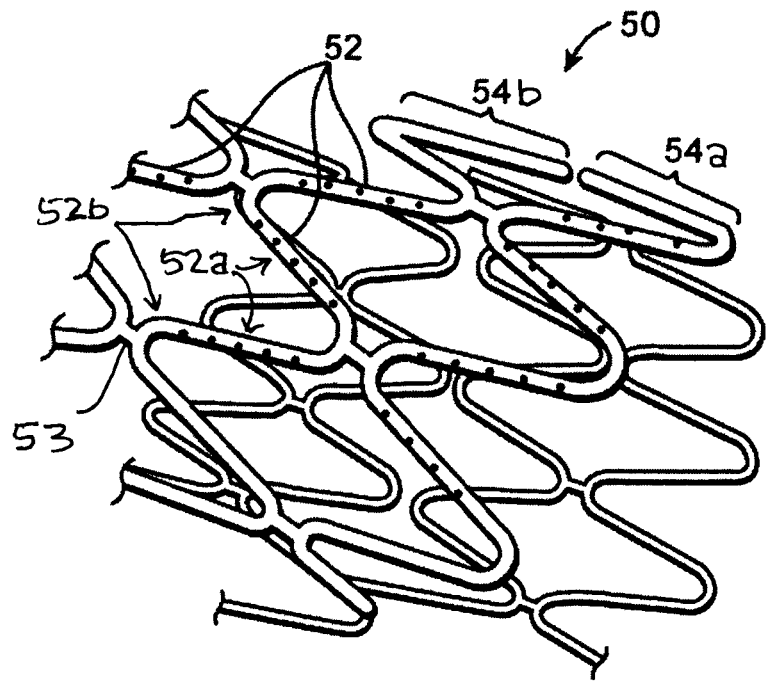
FIG. 1 is a perspective view of a portion of an implantable prosthesis.

As used herein, any term of approximation such as, without limitation, near, about, approximately, substantially, essentially and the like mean that the word or phrase modified by the term of approximation need not be exactly that which is written but may vary from that written description to some extent. The extent to which the description may vary will depend on how great a change can be instituted and have a person of ordinary skill in the art recognize the modified version as still having the properties, characteristics and capabilities of the modified word or phrase. For example, and without limitation, a feature that is described as "substantially equal" to a second feature encompasses the features being exactly equal and the features being readily recognized by a person of ordinary skilled in the art as being equal although the features are not exactly equal.

As used herein, "implantable prosthesis" is a device that is totally or partly introduced, surgically or medically, into a patient's body (animal and human). The duration of implantation may be essentially permanent, i.e., intended to remain in place for the remaining lifespan of the patient; until the device biodegrades; or until the device is physically removed. Examples of implantable prostheses include without limitation self-expandable stents, balloon-expandable stents, grafts, and stent-grafts.

As used herein, a "therapeutic agent" refers to any substance that, when administered in a therapeutically effective amount to a patient suffering from a disease or condition, has a therapeutic beneficial effect on the health and well-being of the patient (animal and human). A therapeutic beneficial effect on the health and well-being of the patient includes, but is not limited to: slowing the progress of a disease or medical condition; causing a disease or medical condition to retrogress; and alleviating a symptom of a disease or medical condition.

As used herein, a "therapeutic agent" includes a substance that when administered to a patient, known or suspected of being particularly susceptible to a disease, in a prophylactically effective amount, has a prophylactic beneficial effect on the health and well-being of the patient. A prophylactic beneficial effect on the health and well-being of a patient includes, but is not limited to: (1) preventing or delaying on-set of the disease or medical condition in the first place; (2) maintaining a disease or medical condition at a retrogressed level once such level has been achieved by a therapeutically effective amount of a substance, which may be the same as or different from the substance used in a prophylactically effective amount; and (3) preventing or delaying recurrence of the disease or condition after a course of treatment with a therapeutically effective amount of a substance, which may be the same as or different from the substance used in a prophylactically effective amount, has concluded. Also, the phrase "therapeutic agent" includes substances useful for diagnostics. The phrase "therapeutic agent" includes pharmaceutically acceptable, pharmacologically active derivatives of those agents specifically mentioned herein, including, but not limited to, salts, esters, amides, and the like.

Referring now in more detail to the exemplary drawings for purposes of illustrating exemplary embodiments of the invention, wherein like reference numerals designate corresponding or like elements among the several views, there is shown in FIG. 1 a portion of exemplary implantable prosthesis 50. The implantable prosthesis includes a plurality of interconnected struts 52. Struts 52 form undulating rings 54 that are connected to each other.

Figure 2:
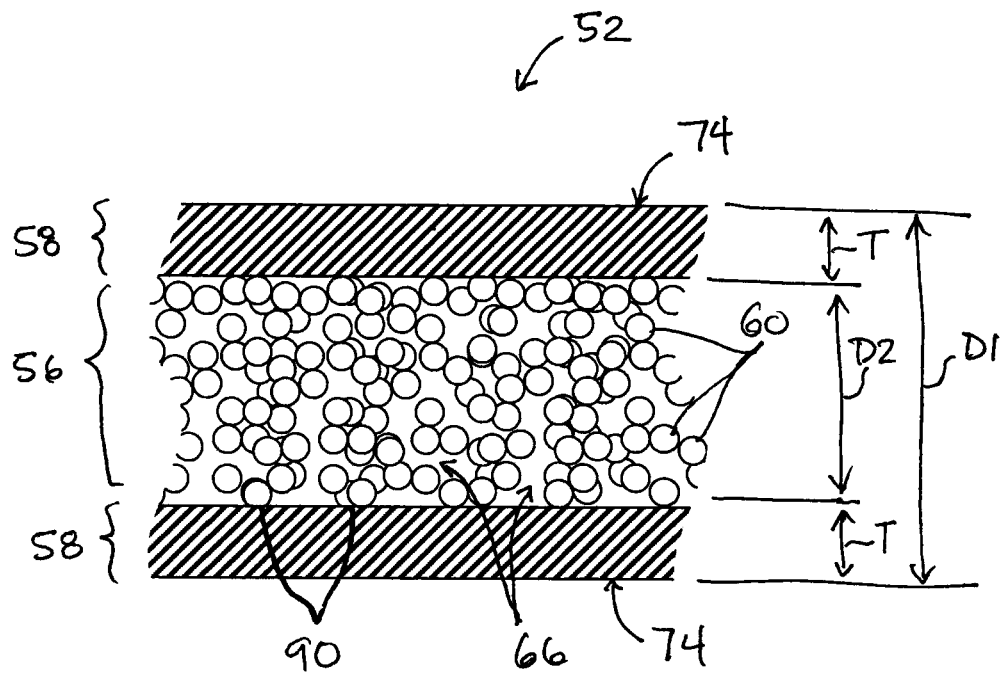
FIG. 2 is a cross-section view of a hollow strut of the implantable prosthesis of FIG. 1, showing radiopaque particles in a lumen of the strut.

As shown in FIG. 2, one or more of struts 52 is hollow. Hollow strut 52 has lumen 56 and metal layer 58 that surrounds lumen 56. Radiopaque particles 60 are disposed with lumen 56.

In some embodiments, struts 52 have outer diameter D1 from about 0.06 mm to about 0.3 mm.

In some embodiments, struts 52 have inner diameter D2 from about 0.01 mm to about 0.25 mm. Inner diameter D2 corresponds to the diameter of lumen 56.

In some embodiments, metal layer 58 has thickness T of about 0.01 mm or greater.

Other outer diameters, inner diameters, and thicknesses can be used. The selected dimension can depend on the type of implantable prosthesis and where the prosthesis is intended to be implanted in a patient.

Figure 3A:
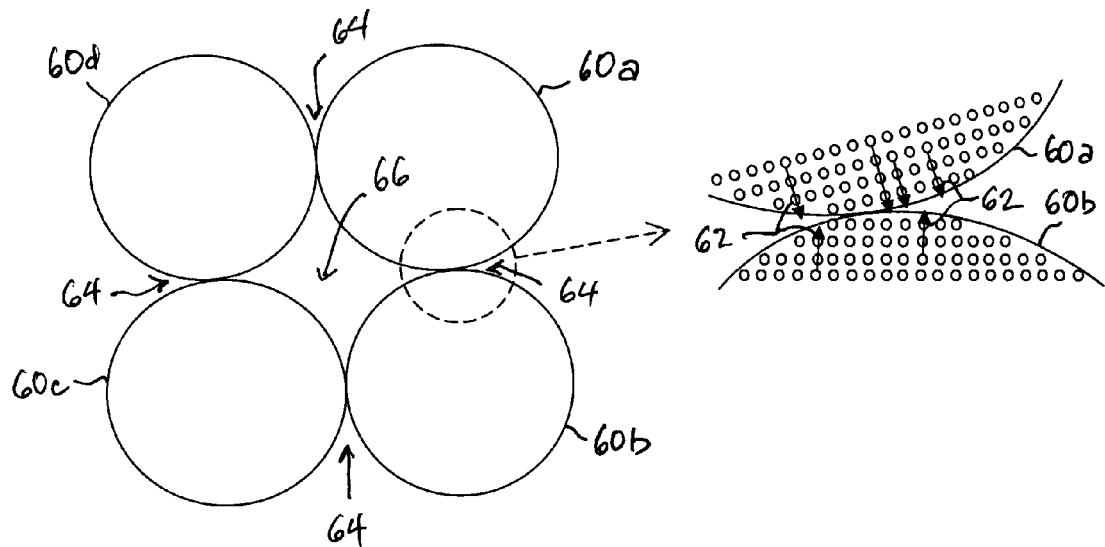
FIG. 3A is a diagram of adjoining radiopaque particles within a lumen of a hollow strut, showing a partial enlarged view of a contact between two adjoining radiopaque particles.
Figure 3B:
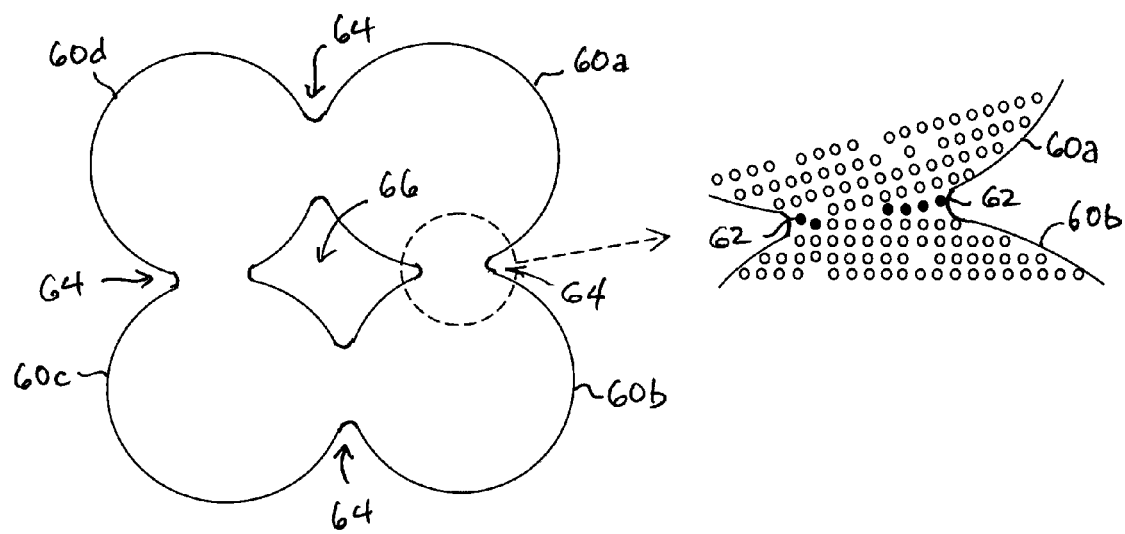
FIG. 3B is a diagram of adjoining radiopaque particles within a lumen of a hollow strut, showing a partial enlarged depiction of atomic diffusion which has bonded two adjoining radiopaque particles.

As shown in FIGS. 3A and 3B, in some embodiments radiopaque particles 60 are bonded directly to each other by diffusion of atoms 62 from adjoining radiopaque particles 60a, 60b to points of contact 64 between adjoining radiopaque particles 60a, 60b. FIG. 3A shows radiopaque particles 60 before bonding by diffusion of atoms 62 to points of contact 64. FIG. 3B shows radiopaque particles 60 after bonding by diffusion of atoms 62 to points of contact 64. Atoms 62 in FIG. 3B which are illustrated in relatively dark shading are the atoms that have diffused to points of contact 64. Points of contact 64 are separated from each other by gaps 66 between radiopaque particles 60.

Figure 4:
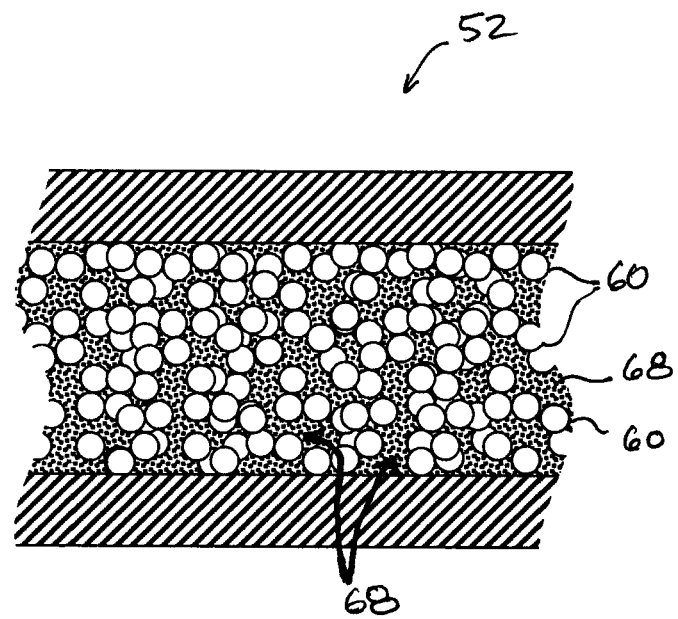
FIG. 4 is a cross-section view of a hollow strut of an implantable prosthesis, showing a therapeutic agent between radiopaque particles.

As shown in FIG. 4, in some embodiments therapeutic agent 68 is contained within gaps 66 (FIG. 2) between radiopaque particles 60.

Figure 5:
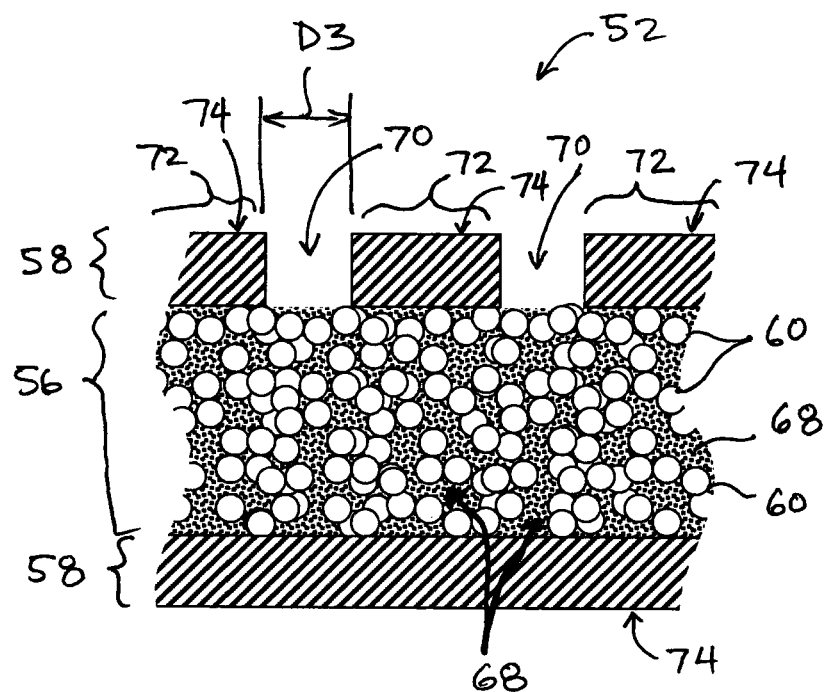
FIG. 5 is a cross-section view of a hollow strut of an implantable prosthesis, showing holes through which a therapeutic agent can be released after implantation.
Figure 6:
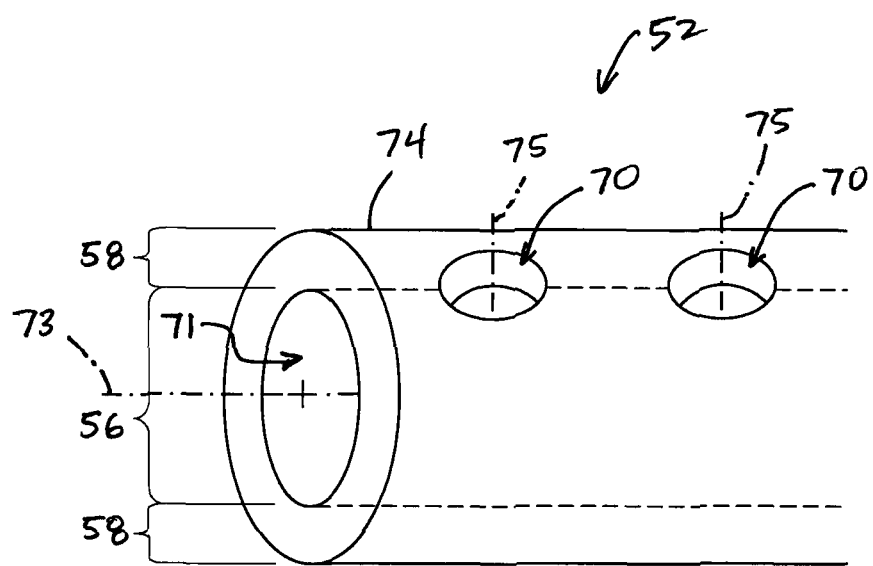
FIG. 6 is a perspective view of a hollow strut of an implantable prosthesis, showing holes through which a therapeutic agent can be released after implantation.

As shown in FIGS. 5 and 6, in some embodiments metal layer 58 has side holes 70 for releasing therapeutic agent 68 out of lumen 56. Side holes 70 are at predetermined locations in metal layer 58. Surface areas 72 of metal layer 58 between side holes 70 are non-porous with respect to therapeutic agent 68.

In some embodiments, side holes 70 have a diameter D3 (FIG. 5) that is greater than that of radiopaque particles 60. For example, the diameter of side holes 70 can be greater than 25 micrometers when radiopaque particles have a diameter not greater than 25 micrometers. Other diameters for side holes 70 can be used. Radiopaque particles 60 are retained in lumen 56 due to the radiopaque particles being directly bonded to each other (such as by sintering), due to an external binder (such as a polymer binder) carrying the radiopaque particles, or both due to the radiopaque particles being directly bonded to each other and an external binder carrying the radiopaque particles.

In some embodiments, side holes 70 have a diameter that is less than that of radiopaque particles 60, so that radiopaque particles 60 remain trapped in lumen 56 after implantation in a patient. Since radiopaque particles 60 cannot pass through side holes 70, radiopaque particles 60 can be introduced into lumen 56 through end hole 71 (FIG. 6) of strut 52. For example, the diameter of side holes 70 can be less than 20 micrometers when radiopaque particles have a diameter of at least 20 micrometers. Other diameters for side holes 70 can be used.

End hole 71 is in communication with lumen 56. In some embodiments, lumen 56 extends through a plurality of struts of prosthesis 50. In some embodiments, lumen 56 extends through all the struts of prosthesis 50.

End hole 71 is located at the free end of strut 52 and has central axis 73 substantially parallel or coaxial with that of lumen 56. Side holes 70 are not located at free end of strut 52. Sides holes 70 have central axes 75 that are substantially non-parallel with that of lumen 56. In FIG. 6, central axes 75 are substantially perpendicular to the central axis of lumen 56. Other non-zero angles can be used between central axes 75 and the central axis of lumen 56.

In some embodiments, side holes 70 are in the shape of either an elongated slot or an oval, so that side holes 70 have a minor diameter and a major diameter. The minor diameter is less than the diameter of radiopaque particles 60, and the major diameter is greater than the diameter of radiopaque particles 60. Slot-shaped or oval-shaped side holes 70 can reduce or prevent clogging of side holes 70 by radiopaque particles 60.

In some embodiments, side holes 70 are located exclusively on an abluminal surface of implantable prosthesis 50. The abluminal surface faces radially outward from the center of the prosthesis and supports or contacts biological tissue when implanted within an anatomical lumen, such as a blood vessel. For example, holes located through the abluminal surface allow therapeutic agent 68 to be released directly into and provide a therapeutic effect to the biological tissue adjoining implantable prosthesis 50.

In some embodiments, side holes 70 are located exclusively on a luminal surface of implantable prosthesis 50. The luminal surface faces radially inward toward the center of the prosthesis and faces the central passageway of the anatomical lumen. For example, holes located through the luminal surface allow therapeutic agent 68 to be released into the blood stream and provide a therapeutic effect downstream of implantable prosthesis 50.

In some embodiments, side holes 70 are located on an abluminal surface and a luminal surface of implantable prosthesis 50.

In some embodiments, radiopaque particles 60 are bonded directly to metal layer 58.

In some embodiments, direct bonding is achieved in a manner similar to what was described above in connection with FIGS. 3A and 3B, so that radiopaque particles 60 are bonded to metal layer 58 by diffusion of atoms from radiopaque particles 60 to points of contact 90 (FIG. 2) between radiopaque particles 60 and the metal layer 58.

In some embodiments, radiopaque particles 60 are bonded directly to each other without requiring an external binder, adhesive, or similar material. An external binder, adhesive, or similar material is not a part of or contained within radiopaque particles 60 and is a material that is added to or mixed with radiopaque particles 60 for the primary purpose of keeping radiopaque particles 60 trapped within lumen 56.

In some embodiments, radiopaque particles 60 that are bonded directly to each other (as in FIGS. 3B, 4 and 5) have no external binder, adhesive, or similar material located between radiopaque particles 60.

In some embodiments, radiopaque particles 60 that are bonded directly to each other are also held together by an external binder, adhesive, or similar material surrounding radiopaque particles 60. The external binder, adhesive, or similar material provides additional strength to the interconnection among radiopaque particles 60.

Figure 7:
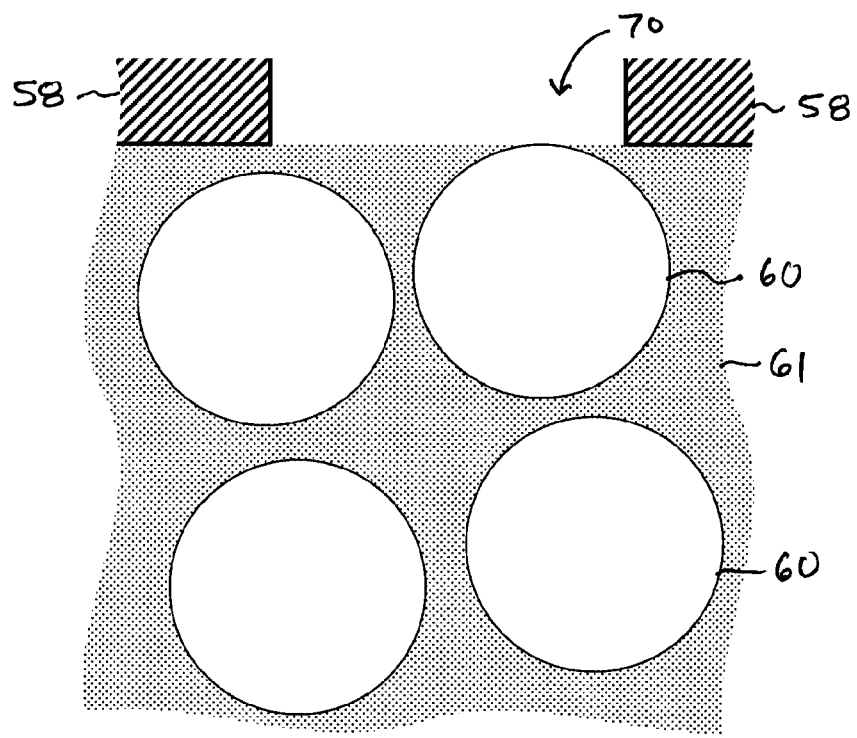
FIG. 7 is a cross-section view of a hollow strut, showing radiopaque particles retained in the strut by an external binder, adhesive, or similar material.

As shown in FIG. 7, in some embodiments radiopaque particles 60 are not retained in lumen 56 by sintering or by atomic diffusion. Radiopaque particles 60 are held inside lumen 56 by an external binder, adhesive, or similar material 61 surrounding radiopaque particles 60. For example, a polymer binder can be used as an external binder.

Figure 8:
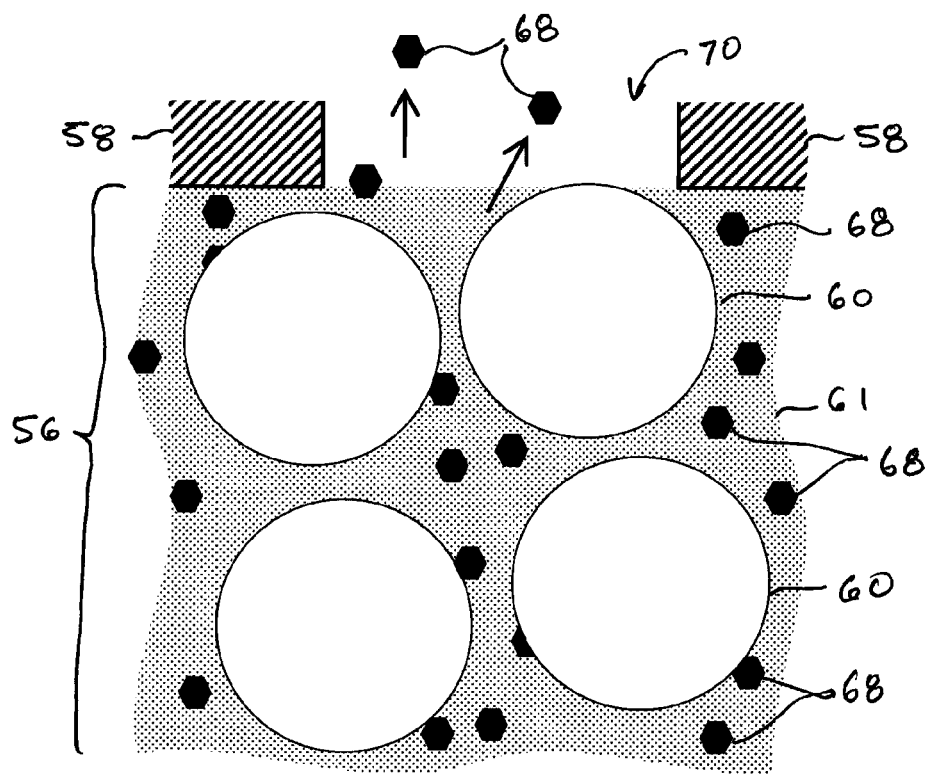
FIG. 8 is a cross-section view of a hollow strut, showing radiopaque particles and therapeutic agents carried by an external binder, adhesive, or similar material.

As shown in FIG. 8, in some embodiments polymer binder 61 carries therapeutic agent 68 and radiopaque particles 60. In some embodiments, polymer binder 61 is combined with therapeutic agent 68.

In some embodiments, polymer binder 61 keeps radiopaque particles 60 from escaping from lumen 56 after implantation in a patient and allows therapeutic agent 68 to diffuse out of polymer binder 61 and escape lumen 56 by passing through side holes 70 after implantation. Polymer binder 61 is biostable and durable when exposed to bodily fluids, such as blood, and substantially remains in lumen 56 after implantation.

In some embodiments, polymer binder 61 is bioabsorbable, biodegradable, or bioerodible. After a substantial period of time, polymer binder 61 does not remain in lumen 56. Radiopaque particles 60 can be retained in lumen 56 by having side holes 70 that are smaller in size than radiopaque particles 60.

The terms "biodegradable," "bioabsorbable," and "bioerodible" are used interchangeably and refer to polymers that are capable of being completely degraded and/or eroded when exposed to bodily fluids such as blood and can be gradually resorbed, absorbed, and/or eliminated by the body. The processes of breaking down and eventual absorption and elimination of the polymer can be caused by, for example, hydrolysis, metabolic processes, enzymolysis, oxidation, bulk or surface erosion, and the like. The word "biostable" refers to a polymer that is not biodegradable.

In some embodiments, therapeutic agent 68 can be carried within polymer binder 61 as discrete solid particles or discrete semi-solid particles. Therapeutic agent 68 can be in the form of powder particles.

In some embodiments, therapeutic agent 68 can be carried within polymer binder 61 as discrete liquid droplets.

In some embodiments, therapeutic agent 68 is carried within polymer binder 61 and is not in the form of discrete particles or discrete droplets within polymer binder 61.

In some embodiments, therapeutic agent 68 is dissolved in polymer binder 61. A solution of therapeutic agent 68 and polymer binder 61 is disposed between radiopaque particles 60.

In some embodiments, polymer binder 61 includes a binder material selected from the group consisting of a phosphorylcholine-based polymer, BioLinx™ polymer (available from Medtronic of Minneapolis, Minn.), poly(n-butyl methacrylate), poly(n-hexyl methacrylate), and styrene-isobutylene-styrene triblock copolymer. An example of a phosphorylcholine-based polymer includes without limitation PC1036. PC1036 is composed of the monomers 2-methacryloyloxyethyl phosphorylcholine (MPC), lauryl methacrylate (LMA), hydroxypropyl methacrylate (HPMA), and trimethoxysilylpropyl methacrylate (TSMA) in the molar ratios of $MPC_{23}$, $LMA_{47}$, $HPMA_{25}$, and $TSMA_5$. BioLinx™ polymer may comprise a blend of a hydrophilic C19 polymer, a water-soluble polyvyle pyrolidinone (PVP), and a lipophilic/hydrophobic C10 polymer. Other binder materials can be used.

In other embodiments, polymer binder 61 includes a binder material selected from polyurethanes, polyphosphazenes, silicones, polyesters, polyolefins, polyisobutylene and ethylene-alphaolefin copolymers, acrylic polymers and copolymers, vinyl halide polymers and copolymers, poly(vinyl chloride), poly(vinyl fluoride), poly(vinylidene fluoride) (PVDF), poly(vinylidene chloride), poly(vinylidene fluoride-co-hexafluoropropylene) (PVDF-HFP), poly(tetrafluoroethylene-co-vinylidene fluoride-co-hexafluoropropylene), polyvinyl ethers, such as polyvinyl methyl ether, polyacrylonitrile, polyvinyl ketones, polyvinyl aromatics, such as polystyrene, polyvinyl esters, such as poly(vinyl acetate), copolymers of vinyl monomers with each other and olefins, such as ethylene-methyl methacrylate copolymers, acrylonitrile-styrene copolymers, ABS resins, and ethylene-vinyl acetate copolymers, polyamides, such as Nylon 66 and polycaprolactam, alkyd resins, polycarbonates, polyoxymethylenes, polyimides, polyethers, poly(sec-butyl methacrylate), poly(isobutyl methacrylate), poly(tert-butyl methacrylate), poly(n-propyl methacrylate), poly(isopropyl methacrylate), poly(ethyl methacrylate), poly(methyl methacrylate), epoxy resins, poly(vinyl butyral), poly(ether urethane), poly(ester urethane), poly(urea urethane), poly(silicone urethane), polyurethanes, rayon, rayon-triacetate, cellulose acetate, cellulose butyrate, cellulose acetate butyrate, cellophane, cellulose nitrate, cellulose propionate, cellulose ethers, carboxymethyl cellulose, polyethers such as poly(ethylene glycol) (PEG), copoly(ether-esters) (e.g. polyalkylene oxides such as poly(ethylene oxide), polypropylene oxide), poly(ether ester), polyalkylene oxalates, polyphosphazenes, poly(fluorophosphazene), poly(phosphoryl choline methacrylate), poly(aspirin), polymers and co-polymers of hydroxyl bearing monomers such as 2-hydroxyethyl methacrylate (HEMA), hydroxypropyl methacrylate (HPMA), hydroxypropylmethacrylamide, PEG acrylate (PEGA), PEG methacrylate, carboxylic acid bearing monomers such as methacrylic acid (MA), acrylic acid (AA), alkoxymethacrylate, alkoxyacrylate, and 3-trimethylsilylpropyl methacrylate (TMSPMA), poly(styrene-isoprene-styrene)-PEG (SIS-PEG), polystyrene-PEG, polyisobutylene-PEG, poly(methyl methacrylate)-PEG (PMMA-PEG), polydimethylsiloxane-co-PEG (PDMS-PEG), PLURONIC™ surfactants (polypropylene oxide-co-polyethylene glycol), poly(tetramethylene glycol), and hydroxy functional poly(vinyl pyrrolidone), In other embodiments, polymer binder 61 may be a material that is biodegradable, bioresorbable, or bioerodible. With such a binder, the radiopaque particles are retained within lumen 56 by their size, or by being bonded to one another or to metal layer 58. Such biodegradable binders include poly(ester amide), polyhydroxyalkanoates (PHA), poly(3-hydroxyalkanoates) such as poly(3-hydroxypropanoate), poly(3-hydroxybutyrate), poly(3-hydroxyvalerate), poly(3-hydroxyhexanoate), poly(3-hydroxyheptanoate) and poly(3-hydroxyoctanoate), poly(4-hydroxyalkanaote) such as poly(4-hydroxybutyrate), poly(4-hydroxyvalerate), poly (4-hydroxyhexanote), poly(4-hydroxyheptanoate), poly(4-hydroxyoctanoate) and copolymers including any of the 3-hydroxyalkanoate or 4-hydroxyalkanoate monomers described herein or blends thereof, poly(D,L-lactide), poly (L-lactide), polyglycolide, poly(D,L-lactide-co-glycolide), poly(L-lactide-co-glycolide), polycaprolactone, poly(lactide-co-caprolactone), poly(glycolide-co-caprolactone), poly(dioxanone), poly(ortho esters), poly(anhydrides), poly (tyrosine carbonates) and derivatives thereof, poly(tyrosine ester) and derivatives thereof, poly(imino carbonates), poly (glycolic acid-co-trimethylene carbonate), polyphosphoester, polyphosphoester urethane, poly(amino acids), polycyanoacrylates, poly(trimethylene carbonate), poly (iminocarbonate), poly(glyceryl sebacate), polypropylene fumarate), poly(ethylene oxide/poly(lactic acid) (PEO/PLA), polycaprolactone-PEG (PCL-PEG), PLA-PEG, biomolecules such as chitosan, alginate, fibrin, fibrinogen, cellulose, starch, dextran, dextrin, fragments and derivatives of hyaluronic acid, heparin, fragments and derivatives of heparin, glycosamino glycan (GAG), GAG derivatives, polysaccharide, chitosan, alginate, or combinations thereof.

In some embodiments, the copolymer described herein can exclude any one or more of the aforementioned polymers.

As used herein, the terms poly(D,L-lactide), poly(L-lactide), poly(D,L-lactide-co-glycolide), and poly(L-lactide-co-glycolide) can be used interchangeably with the terms poly(D,L-lactic acid), poly(L-lactic acid), poly(D,L-lactic acid-co-glycolic acid), or poly(L-lactic acid-co-glycolic acid), respectively. In some embodiments, the binder material of polymer binder 61 is selected based on the type of therapeutic agent that is intended to diffuse out of the polymer binder.

Metal layer 58 can be made of any biocompatible material suitable for implantation in a human or animal body. In some embodiments, metal layer 58 comprises a base material selected from the group consisting of 316L stainless steel, CoNi MP35N, CoCr L-605, and FePtCr. Other base materials can be used.

In some embodiments, the base material of metal layer 58 has a melting temperature that is either greater than or about the same as that of radiopaque particles 60.

In some embodiments, metal layer 58 is not formed from sintered particles of the base material, so that metal layer 58 does not have a randomly pitted texture or granular texture which could result from sintering.

In some embodiments, exterior surfaces 74 (FIGS. 2 and 5) of metal layer 58 are substantially smooth. Exterior surfaces 74 can have a polished finish.

In some embodiments, exterior surfaces 74 of metal layer 58 are maintained in a bare metal state. When in a bare metal state, there is no non-metal coating present on exterior surfaces 74.

In some embodiments, no coating containing a therapeutic agent is present on exterior surfaces 74 of metal layer 58.

Radiopaque particles 60 can be made of any material suitable for implantation in a human or animal body. Radiopaque materials are those materials with high density, or high atomic number that efficiently absorb x-ray radiation. In some embodiments, radiopaque particles 60 comprise a radiopaque material selected from the group consisting of gold, Au/Pt/Zn 85/10/5 alloy, Au/Ag/Pt/Zn 73/12/0.5/15 alloy, platinum, iridium, platinum/iridium alloys, palladium, tantalum, and niobium. Other radiopaque materials can be used.

In some embodiments, radiopaque particles 60 can have a diameter from about 10 nanometers to about 25 micrometers. Other diameters for radiopaque particles 60 can be used.

Referring again to FIG. 1, struts 52 form diamond-shaped cells. It should be understood that many strut configurations, in addition to the configuration shown in FIG. 1, are possible. For example, struts of an implantable prosthesis of the present invention can form other cell shapes. Strut configurations include those shown and described in U.S. Pat. No. 5,514,154 to Lau et al., entitled "Expandable Stents," which is incorporated herein by reference in its entirety for all purposes. As a further example, the strut of an implantable prosthesis of the present invention can be helical or a coil. A plurality of helical- or coil-shaped struts can be welded together or joined by other methods to form an implantable prosthesis.

Figure 9:
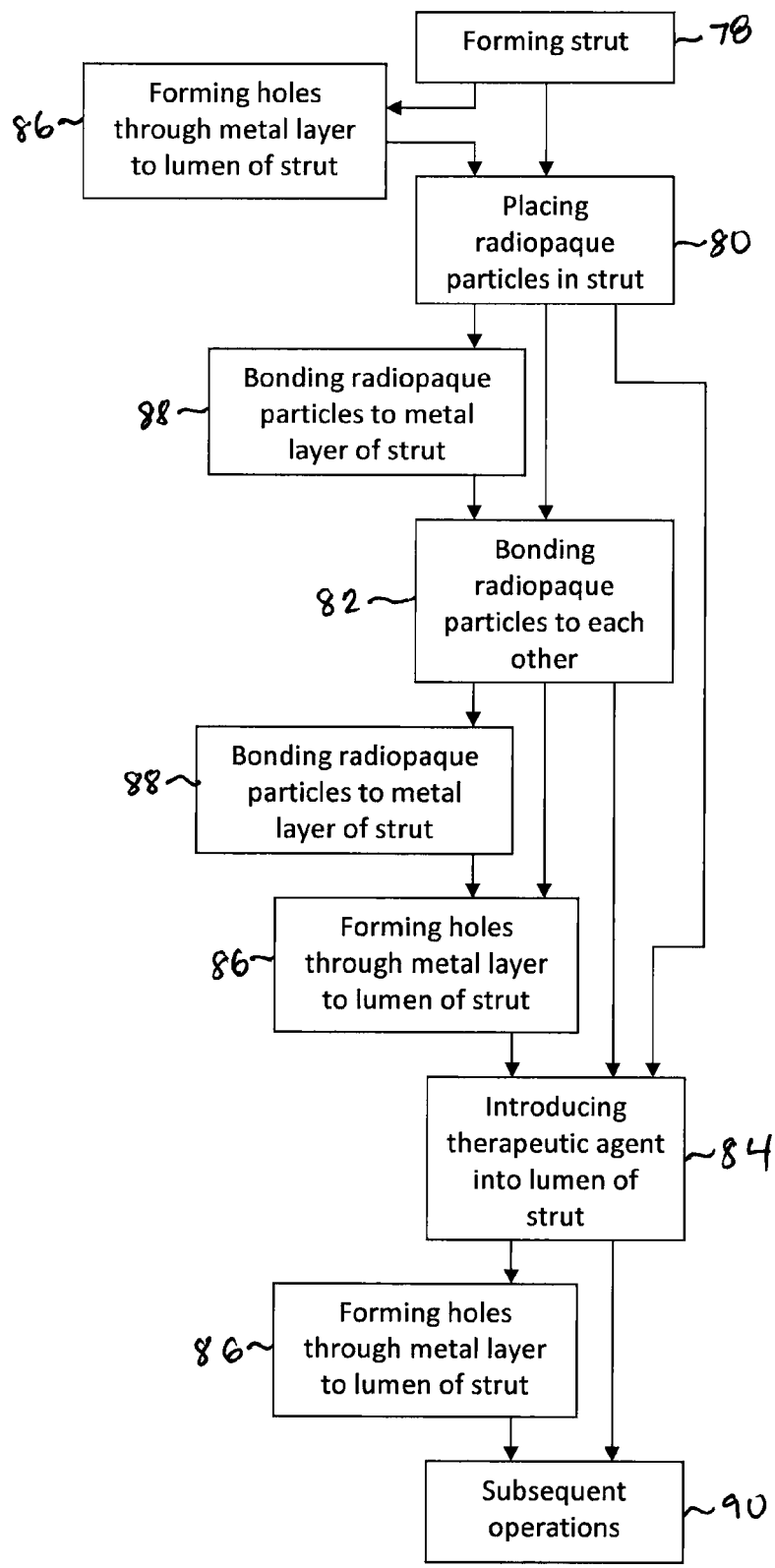
FIG. 9 is a flow diagram of an exemplary method of making an implantable prosthesis.

As shown in FIG. 9, an exemplary method for making an implantable prosthesis includes placing radiopaque particles 60 within lumen 56 of strut 52 (block 80), and optionally followed by bonding radiopaque particles 60 to each other (block 82).

In some embodiments, radiopaque particles 60 include a radiopaque material and an internal binder. The internal binder is contained within and is part of radiopaque particles 60. The internal binder holds the radiopaque material together so as to form radiopaque particles or clumps.

In some embodiments, the placing (block 80) of radiopaque particles 60 within lumen 56 includes placing a mixture of radiopaque particles 60 and an external binder, adhesive, or similar material, or a mixture of radiopaque particles 60, therapeutic agent 68, and an external binder, adhesive, or similar material. The external binder, adhesive, or similar material 61 can be as described above in connection with FIGS. 7 and 8. The external binder, adhesive, or similar material 61 can be a polymer binder as described above. In some embodiments, the mixture is introduced into lumen 56 by passing the mixture through end hole 71 (FIG. 6) of strut 52. After the mixture is introduced, side holes 70 can be made through strut 52 to allow any therapeutic agent to diffuse out of external binder 61. Optionally, end hole 71 is sealed after the mixture is introduced.

In some embodiments, the mixture is introduced into lumen 56 by passing the mixture through side holes 70 (FIG. 6) of strut 52. Side holes 70 are made for the purpose of loading lumen 56 with the mixture containing external binder 61 and for purpose of allowing any therapeutic agent to diffuse out of external binder 61 and escape from lumen 56.

In some embodiments, the external binder, adhesive, or similar material 61 is added into lumen 56 after the placing (block 80) of radiopaque particles 60 within lumen 56. The adding of external binder, adhesive, or similar material 61 can be performed by immersing strut 52 in material 61 or by injecting material 61 in an opening at an end or side of strut 52. Material 61 can be a polymer binder as described above in connection with FIGS. 7 and 8.

In some embodiments, the material (which is added into lumen 56 after the placing (block 80) of radiopaque particles 60 within lumen 56) is a mixture of a polymer binder and therapeutic agent 68.

In some embodiments, the material (which is added into lumen 56 after the placing (block 80) of radiopaque particles 60 within lumen 56) is a polymer binder capable of absorbing therapeutic agent 68. After the polymer binder is in lumen 56, therapeutic agent 68 is allowed to infuse the polymer binder prior to implantation. Strut 52 can be immersed in a container containing therapeutic agent 68. After implantation, therapeutic agent 68 is allowed to diffuse out of the polymer binder and escape out of lumen 56.

In some embodiments, the placing (block 80) of radiopaque particles 60 within lumen 56 includes placing into lumen 56 a mixture of radiopaque particles 60 and a sintering additive. The sintering additive is mixed together with radiopaque particles 60 prior to placing the mixture into lumen 56. The sintering additive can facilitate subsequent sintering.

In some embodiments, the sintering additive has a melting temperature that is less than that of radiopaque particles 60.

In some embodiments, the bonding (block 82) includes sintering the radiopaque particles together. During sintering, strut 52 containing radiopaque particles 60 is placed in a chamber of an oven having an internal temperature that is carefully controlled. The oven internal temperature is raised to a sintering temperature.

In some embodiments, the sintering temperature is from about 500° C. to about 670° C. Other sintering temperatures can be used.

In some embodiments, the sintering temperature is above 20° C. (68° F.) and is below the melting temperature of metal layer 58. Examples of melting temperatures of metal layer 58 include without limitation those listed in TABLE 1.

TABLE 1

| Material for Metal Layer | Softening Temperature | Melting Temperature |
|---|---|---|
| 316L Stainless Steel | Max use of 870° C. | 1390° C. to 1440° C. |
| CoNi MP35N | — | 1316° C. to 1441° C. |
| CoCr L-605 | Max use of 980° C. | 1330° C. to 1410° C. |

In some embodiments, the sintering temperature is above 20° C. (68° F.) and is at or below the softening temperature of metal layer 58. Examples of softening temperatures of metal layer 58 include without limitation those listed in TABLE 1.

In some embodiments, the sintering temperature is below the melting temperature of radiopaque particles 60. Examples of melting temperatures of radiopaque particles 60 include without limitation those listed in TABLE 2.

TABLE 2

| Material for Radiopaque Particles | Softening Temperature | Melting Temperature |
|---|---|---|
| Gold | 1064° C. | 1064° C. |
| Au/Pt/Zn 85/10/5 Alloy | 940° C. | 990° C. |
| Au/Ag/Pt/Zn 73/12/0.5/15 Alloy | 670° C. | 700° C. |

In some embodiments, the sintering temperature is above 20° C. (68° F.) and is at or below the softening temperature of radiopaque particles 60. Examples of softening temperatures of radiopaque particles 60 include without limitation those listed in TABLE 2.

In some embodiments, after sintering, radiopaque particles 60 have not completely coalesced or merged with each other, and they remain distinct from each other (see, for example, FIG. 3B). Radiopaque particles 60 form a granular and porous structure, which can be achieved by using a sintering temperature, such as any of the softening temperatures in TABLE 2, that does not completely liquefy radiopaque articles 60.

In some embodiments, the sintering temperature is below the melting temperature of radiopaque particles 60 and is at or above the melting temperature of a sintering additive which is contained with lumen 56 and mixed with radiopaque particles 60.

Still referring to FIG. 9, in some embodiments the bonding (block 82) includes causing diffusion of atoms from adjoining radiopaque particles to points of contact between the adjoining radiopaque particles. The diffusion of atoms can be facilitated by exposing the adjoining radiopaque particles 60a, 60b (FIG. 3A) to an elevated temperature above 20° C. (68° F.). An example of an elevated temperature includes without limitation a sintering temperature as described above.

In some embodiments, the bonding (block 82) includes allowing points of contact 64 to be separated by gaps 66 (FIG. 3B) between radiopaque particles 60. Gaps 66 between radiopaque particles 60 can be maintained when the elevated temperature is kept below the melting temperature of radiopaque particles 60.

In some embodiments, the placing (block 80) of radiopaque particles 60 within lumen 56 is preceded by forming strut 52 (block 78).

In some embodiments, strut 52 is made from a single, continuous wire which has been meandered or bent to form crests. Welds 53 (FIG. 1) at predetermined locations can be used to provide strength or rigidity at desired locations.

In some embodiments, strut 52 is made according to conventional methods known in the art. For example, strut 52 can be a hollow wire, and forming strut 52 can include conventional process steps for forming hollow wires. As a further example, strut 52 can be made according to process steps described in the above-mentioned publication no. US 2011/0008405, entitled "Hollow Tubular Drug Eluting Medical Devices".

In some embodiments, forming strut 52 (block 78) includes polishing exterior surfaces 74 (FIGS. 2 and 5) to give the exterior surfaces 74 a substantially smooth finish.

Still referring to FIG. 9, in some embodiments the bonding (block 82) is followed by introducing therapeutic agent 68 into lumen 56 and between radiopaque particles 60 (block 84). If radiopaque particles 60 were bonded together at an elevated temperature, the introducing (block 84) is performed after radiopaque particles 60 have cooled below the elevated temperature.

In some embodiments, the introducing (block 84) of therapeutic agent 68 into lumen 56 includes immersing strut 52 in a solution or mixture containing therapeutic agent 68, and allowing therapeutic agent 68 to flow into lumen 56 through an opening at the end or side of strut 52

In some embodiments, the introducing (block 84) of therapeutic agent 68 into lumen 56 includes applying a vacuum (negative pressure) to lumen 56 to draw a solution or mixture of therapeutic agent 68 into lumen 56. Alternatively, or in addition to the vacuum, positive pressure is applied to the solution or mixture from outside strut 52 to force the solution or mixture into lumen 56.

In some embodiments, the introducing (block 84) of therapeutic agent 68 into lumen 56 includes introducing a mixture of therapeutic agent 68 and a carrier substance. The carrier substance can be a solvent, a polymer, or a combination thereof. The carrier substance can facilitate transportation of therapeutic agent 68, movement of therapeutic agent 68 between radiopaque particles 60, and/or control the release of therapeutic agent 68 out of lumen 56. Selection of the carrier substance can depend on the type of therapeutic agent it is intended to carry.

In some embodiments, the carrier substance is a polymer binder. The polymer binder can be as described above in connection to FIGS. 7 and 8. The polymer binder can set or cure after it is introduced into lumen 56. After setting or curing, therapeutic agent 68 diffuses or elutes out of the polymer binder and escapes from lumen 56. After setting or curing, the polymer binder prevents radiopaque particles 60 from shifting in position with lumen 56 and prevents radiopaque particles 60 from escaping out of an end hole 71 or out of side holes 70 which are larger than radiopaque particles 60.

In some embodiments, side holes 70 (FIGS. 5-8) can be formed (block 86) at predetermined locations through metal layer 58 that surrounds lumen 56. Forming the holes can be performed either before or after the introducing (block 84) of the therapeutic agent 68 into lumen 56.

In some embodiments, forming (block 86) of side holes 70 is performed before the placing (block 80) radiopaque particles 60 in strut 52.

Holes 70 extend completely through metal layer 58 to allow therapeutic agent 68 to be introduced into lumen 56, or released out from lumen 56 after implantation, or both introduced into and released out from lumen 56.

In some embodiments, side holes 70 are formed (block 86) so that side holes 70 are sized to prevent radiopaque particles 60 from escaping lumen 56 through side holes 70. Side holes 70 can be formed (block 86) before or after the placing (block 80) of radiopaque particles 60 in lumen 56 of strut 52.

In some embodiments, after radiopaque particles 60 particles are placed (block 80) into lumen 56 through end hole 71 (FIG. 6), the end hole can be crimped or plugged or sealed in order to trap radiopaque particles 60 particles in lumen 56. Side holes 70 have a diameter D3 (FIG. 5) that is smaller than a diameter of radiopaque particles 60, which prevents radiopaque particles 60 from escaping lumen 56 through side holes 70.

In some embodiments, in addition to having side holes 70 sized smaller than radiopaque particles 60, radiopaque particles 60 can be bonded indirectly to each other by external binder 61 as described above and/or can be bonded directly to each other by atomic diffusion using a sintering process as described above. External binder 61 and/or sintering provides additional security for retaining radiopaque particles 60 within lumen 56.

In some embodiments, forming strut 52 (block 78) is performed such that surface areas 72 (FIG. 5) of metal layer 58 between holes 70 are non-porous with respect to therapeutic agent 68. Therapeutic agent 68 may pass through holes 70 but not through surface areas 72 between holes 70. Holes 70 can be formed by mechanical drilling, laser drilling, chemical etching, ion beam milling and any combination thereof.

In some embodiments, therapeutic agent 68 is released from lumen 56 when therapeutic agent 68 passes through holes 70 at the predetermined locations.

In some embodiments, the predetermined locations are selected so that holes 70 are at uniform spacing apart from each other. Holes 70 are not randomly distributed.

In some embodiments, the predetermined locations are selected so that holes 70 are located in first and second regions, and are spaced closer to each other at the first region as compared to the second region. For example, the first region and second regions can correspond to different segments of strut 52. First region and second region can be a substantially straight segment 52a (FIG. 1) and a curved segment 52b (FIG. 1), or in reverse order. As a further example, the first region and second regions can correspond to different segments of implantable prosthesis 50. First region and second region can be an end segment 54a (FIG. 1) and a medial segment 54b (FIG. 1) adjacent the end segment, or in reverse order.

Still referring to FIG. 9, in some embodiments the method further includes bonding radiopaque particles 60 to metal layer 58 (block 88). The bonding (block 88) can help avoid release of radiopaque particles 60 out from lumen 56.

The bonding (block 88) of radiopaque particles 60 to metal layer 58 is performed before the introducing (block 84) of therapeutic agent 68 into lumen 56, and can be performed before, during or after the bonding (block 82) of radiopaque particles 60 to each other. The bonding (block 88) can be accomplished by sintering radiopaque particles 60 to metal layer 58.

In some embodiments, the bonding (block 88) of radiopaque particles 60 to metal layer 58 includes causing diffusion of atoms from radiopaque particles 60 to points of contact 90 (FIG. 2) between radiopaque particles 60 and metal layer 58. The diffusion of atoms can be facilitated by exposing radiopaque particles 60 and metal layer 58 to an elevated temperature above 20° C. (68° F.). An example of an elevated temperature includes without limitation a sintering temperature as described above.

In some embodiments, subsequent operations (block 90) optionally includes any one or more of cleaning the outer surface of metal layer 58, applying an outer coating to the outer surface of metal layer 58, crimping of the stent onto a delivery catheter, and sterilization of implantable prosthesis 50.

In some embodiments, an outer coating on metal layer 58 can include any one or a combination of a primer layer, a barrier layer, and a reservoir layer containing a therapeutic agent.

Although reference was made to parts of implantable prosthesis 50 of FIGS. 1-5 in the description of the above method embodiments, it should be understood that the above method embodiments can be performed to make other types and configurations of implantable prostheses.

Examples of therapeutic agents that can be used in various embodiments of the present invention, including the exemplary embodiments described above, include without limitation an anti-restenosis agent, an antiproliferative agent, an anti-inflammatory agent, an antineoplastic, an antimitotic, an antiplatelet, an anticoagulant, an antifibrin, an antithrombin, a cytostatic agent, an antibiotic, an anti-enzymatic agent, an angiogenic agent, a cyto-protective agent, a cardioprotective agent, a proliferative agent, an ABC A1 agonist, an antioxidant, a cholesterol-lowering agent, aspirin, an angiotensin-converting enzyme, a beta blocker, a calcium channel blocker, nitroglycerin, a long-acting nitrate, a glycoprotein IIb-IIIa inhibitor or any combination thereof.

Examples of polymers that can be used in various embodiments of the present invention, including the exemplary embodiments described above, include without limitation ethylene vinyl alcohol copolymer (commonly known by the generic name EVOH or by the trade name EVAL™); poly(butyl methacrylate); poly(vinylidene fluoride-co-hexafluoropropylene) (e.g., SOLEF® 21508, available from Solvay Solexis PVDF of Thorofare, N.J.); poly(vinylidene fluoride) (otherwise known as KYNAR™, available from Atofina Chemicals of Philadelphia, Pa.); poly(tetrafluoro-ethylene-co-hexafluoropropylene-co-vinylidene fluoride); ethylene-vinyl acetate copolymers; poly(pyrrolidinone); poly(vinyl pyrrolidinone-co-hexyl methacrylate-co-vinyl acetate); poly(butyl methacrylate-co-vinyl acetate); and polyethylene glycol; and copolymers and combinations thereof.

While several particular forms of the invention have been illustrated and described, it will also be apparent that various modifications can be made without departing from the scope of the invention. It is also contemplated that various combinations or subcombinations of the specific features and aspects of the disclosed embodiments can be combined with or substituted for one another in order to form varying modes of the invention. Accordingly, it is not intended that the invention be limited, except as by the appended claims.

What is claimed is:

1. An implantable prosthesis comprising:
a strut having a lumen;
radiopaque particles within the lumen; and
a biostable polymer binder within the lumen, the polymer binder surrounding the radiopaque particles and retaining the radiopaque particles in the lumen.

2. The implantable prosthesis of claim 1, wherein the radiopaque particles are not bonded directly to each other and the polymer binder is located between and separates the radiopaque particles.

3. The implantable prosthesis of claim 1, wherein the polymer binder prevents the radiopaque particles from escaping through holes in the strut.

4. The implantable prosthesis of claim 1, further comprising a therapeutic agent within the lumen, wherein the polymer binder carries or is combined with the therapeutic agent.

5. The implantable prosthesis of claim 4, wherein the strut includes a metal layer surrounding the lumen, and the metal layer includes a plurality of side holes for releasing the therapeutic agent.

6. The implantable prosthesis of claim 5, wherein surface areas of the metal layer between the side holes are non-porous with respect to the therapeutic agent.

7. The implantable prosthesis of claim 5, wherein the polymer binder allows the therapeutic agent to diffuse or elute out of the polymer binder and escape out of the side holes of the metal layer while the polymer binder simultaneously prevents the radiopaque particles from escaping out of the side holes of the metal layer.

8. The implantable prosthesis of claim 1, wherein the polymer binder prevents the radiopaque particles from shifting in position within the lumen.

9. The implantable prosthesis of claim 1, wherein radiopaque particles include a mixture of a radiopaque material and an internal binder.

* * * * *